United States Patent [19]
Isogai et al.

[11] Patent Number: 5,909,269
[45] Date of Patent: Jun. 1, 1999

[54] OPHTHALMIC APPARATUS

[75] Inventors: Naoki Isogai, Nishio; Mikio Kurachi, Hazu-gun, both of Japan

[73] Assignee: Nidek Co., Ltd., Japan

[21] Appl. No.: 09/021,440

[22] Filed: Feb. 10, 1998

[51] Int. Cl.$^6$ ..................................................... A61B 3/14
[52] U.S. Cl. ....................................................... 351/208
[58] Field of Search .................................. 351/206, 208, 351/211, 210, 209, 221, 204

[56] References Cited

U.S. PATENT DOCUMENTS

| | | | |
|---|---|---|---|
| 5,463,430 | 10/1995 | Isogai et al. | 351/208 |
| 5,735,283 | 4/1998 | Snook | 351/211 |
| 5,844,659 | 12/1998 | Isogai | 351/208 |

FOREIGN PATENT DOCUMENTS

| | | |
|---|---|---|
| 62-253028 | 11/1987 | Japan . |
| 3-184524 | 8/1991 | Japan . |
| 8-224213 | 9/1996 | Japan . |
| 8-322796 | 12/1996 | Japan . |

OTHER PUBLICATIONS

U.S. patent application Ser. No. 08/982,255, filed Dec. 1, 1997, Group Art Unit presently unknown.

*Primary Examiner*—George Manuel
*Attorney, Agent, or Firm*—Finnegan, Henderson, Farabow, Garrett & Dunner, L.L.P.

[57] ABSTRACT

An ophthalmic apparatus comprising a measuring device for inspecting or measuring a patient's eye, a moving device for moving the measuring device relative to the patient's eye, a designating device for designating an eye to be measured, photographing device capable of photographing a face including both eyes, first detecting device for detecting positional relationship between the measuring device and each of right and left eyes respectively based on an image signal from the photographing device, an alignment detecting device for detecting an alignment condition of the measuring device relative to the eye, and a leading device for leading the moving device so that the measuring device may be alined within the predetermined range relative to the eye based on results detected by the first detecting device and the alignment detecting device.

19 Claims, 8 Drawing Sheets

OPHTHALMIC APPARATUS

BACKGROUND OF THE INVENTION

1. Field of the Invention

The present invention relates to an ophthalmic apparatus for inspecting or measuring a patient's eyes and more particularly, to a mechanism for aligning the patient's eye with the apparatus so as to be the predetermined positional relationship

2. Description of Related Art

As an ophthalmic apparatus for inspecting or measuring a patient's eye, such apparatus as a refractive power measuring apparatus, a corneal shape measuring apparatus and the like are well known. This kind of apparatus needs an alignment adjustment which adjusts a position of a measuring part by moving it to vertical and lateral directions, as well as backward and forward directions, relative to the patient's eye.

Most of this kind of apparatus measures each eye one by one, and the alignment adjustment thereof is performed by observing one eye of the patient, which is to be measured by an operators with an observing device of high magnifications then moving the apparatus relative to the patient's eye.

However, a size of a face and a position of an eye of a patient differs with persons, therefore, in case of the alignment adjustment by using the observing device of high magnification, the patient's eye does not always come in observation sight simultaneously at the time of starting alignment. In such case, an operator not skilled in measuring takes much time to perform the alignment adjustment for the patient's eye.

In addition, although such apparatus that aligns a measuring part with a patient's eye automatically is proposed, the detecting range is small, therefore, the alignment adjustment which comes close to the patient's eye needs the operator's (or the examiner's) own operation.

SUMMARY OF THE INVENTION

The present invention has been made in view of the above circumstances and has an object to overcome the above problems and to provide an ophthalmic apparatus by which the alignment adjustment can be performed easily.

Another object of the present invention is to provide an ophthalmic apparatus for which the alignment operation by the operator and the examinee is not necessary.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus comprises measuring means for inspecting or measuring a patient's eye, moving means for moving the measuring means relative to the patient's eye, designating means for designating an eye to be measured, photographing means capable of photographing a face including both eyes of the patient first detecting means for detecting positional relationship between the measuring means and each of right and left eyes respectively based on an image signal from the photographing means, alignment detecting means for detecting an alignment condition of the measuring means relative to the eye, and leading means for leading the moving means so that the measuring means may be alined within the predetermined range relative to the eye based on results detected by the first detecting means and the alignment detecting means.

In another aspect of the present invention, an ophthalmic apparatus comprises measuring means for inspecting or measuring a patient's eye, moving means for moving the measuring means relative to the patient's eye, designating means for designating an eye to be measured, photographing means capable of photographing a face including both eyes of the patient, first detecting means for detecting positional relationship between the measuring means and each of right and left eyes respectively based on an image signal from the photographing means, first controlling means for controlling the moving means so that the measuring means may be alined close to the position of the eye designated by the designating means based on results detected by the first detecting means, target projecting means for projecting an alignment target onto the eye under the condition that the measuring means is aligned close to the position of the eye, second detecting means for detecting an alignment condition of the measuring means relative to the eye by detecting an image of the target projected by the target image projecting means, second controlling means for further controlling the moving means so that the measuring means may be aligned to be capable of measuring based on results detected by the second detecting means, judging means for judging suitability of the alignment based on results detected by the second detecting means, and measurement starting signal generating means for generating a starting signal for measurement, which causes the measuring means to work at the time when it is judged by the judging means that the alignment is appropriate According to the present invention, the alignment adjustment can be performed extremely easily.

Also, according to the present invention, the measurement can be performed without performing the alignment operation by the operator and the patient

BRIEF DESCRIPTION OF THE DRAWINGS

The accompanying drawings, which are incorporated in and constitute a part of this specification, illustrate embodiments of the present invention and, together with the description serve to explain the objects advantages and principles of the invention. In the drawings.

DETAILED DESCRIPTION OF THE PREFERRED EMBODIMENTS

A detailed description of one preferred embodiment of an ophthalmic apparatus embodying the present invention will now be given referring to the accompanying drawings.

Figure 1:
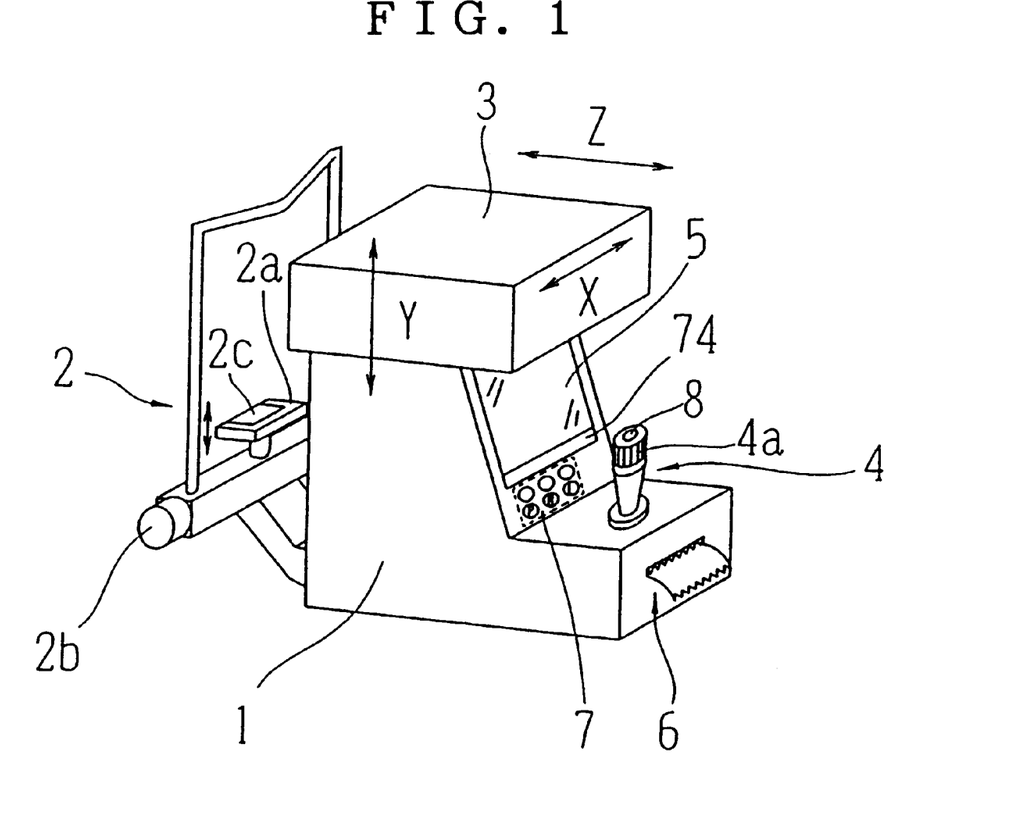
FIG. 1 is an overview of an apparatus of the preferred embodiment of the present invention.

FIG. 1 is an overview of a refractive power measuring apparatus of the preferred embodiment. Reference numeral 1 is a body to which a face-fixing unit 2 for fixing a face of a patient is fixed. A chin rest 2a is held by the face-fixing unit 2 so that it may move to a vertical direction, that is, if a chin knob 2b is rotated, then the chin rest 2a is made to move up and down, thereby a height position of a patient's eye can be adjusted. Also, a chin rest switch 2c is provided for the chin rest 2a, which detects that the face of the patient is put on.

Figure 2:
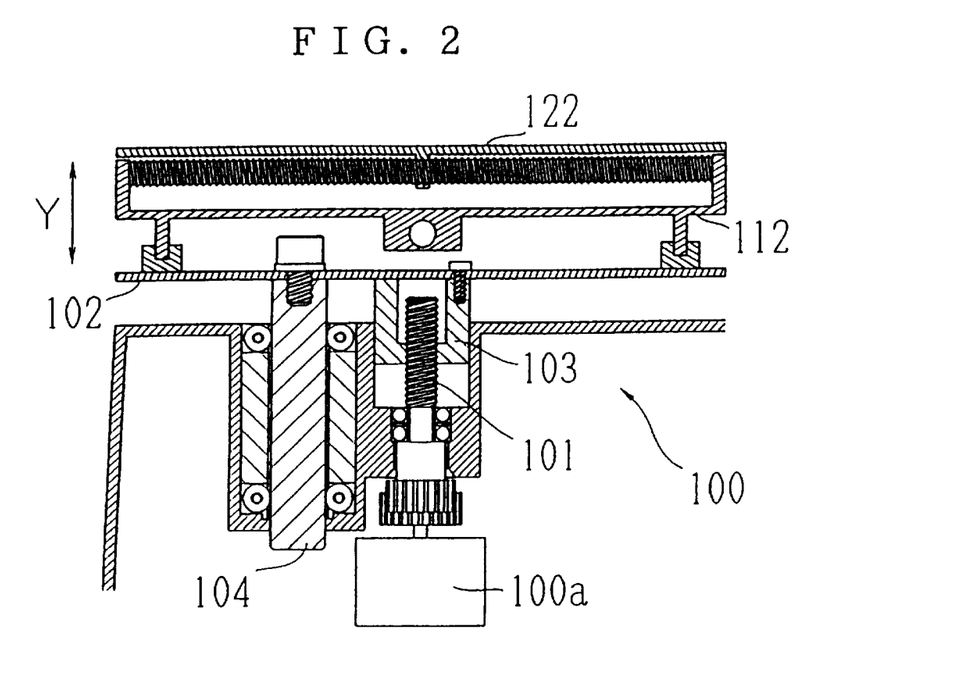
FIG. 2 is a view showing a moving mechanism in Y direction.
Figure 3:
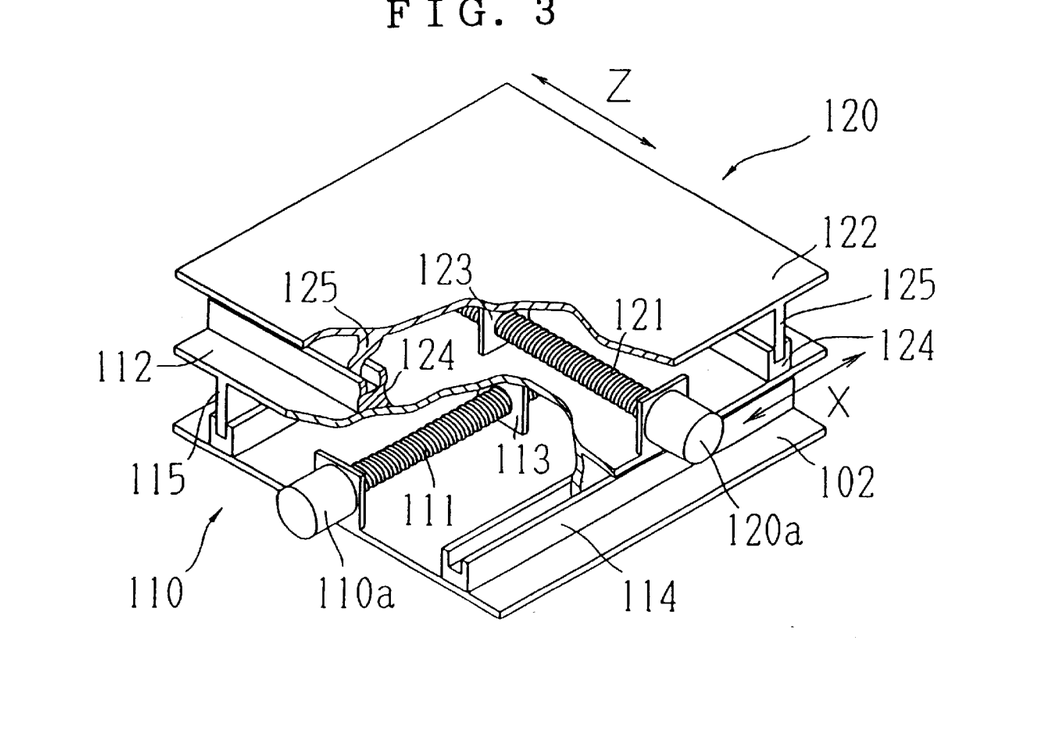
FIG. 3 is a view showing a moving mechanism in X and Z directions.

Reference numeral 3 is a measuring part which holds below-mentioned optical system The measuring part 3 is made to move to Y direction relative to the body 1 by Y-direction (vertical direction) moving mechanism 100 as shown in FIG. 2, and is made to move to X and Z directions relative to the body 1 by X-direction (lateral direction) moving mechanism 110 and Z-direction (backward and forward directions and working distance direction) moving mechanism 120. Y-direction moving mechanism 100 makes a feed screw 101 rotate via a gear by a pulse motor 100a fixed to a side of the body 1, thereby makes a female screw 103 fixed to Y-table 102 move up (down), and allows Y-table 102 to move up and downs 104 is a guide shaft fixed to Y-table 102. X-direction moving mechanism 110 makes a feed screw 111 rotate by a pulse motor 110a fixed to Y-table 102, thereby makes a female screw 113 fixed to X-table 112, move to right and left, and allows X-table 112 to move right and left. 114 is a guide slot fixed to Y-table 102, 115 is a guide shaft fixed to X-table 112. Z-direction moving mechanism 120 has the same construction as X-direction moving mechanism 110, Z-table 122 moves to Z-direction by rotation of a pulse motor 120a.

Referring to such moving mechanism as described above, the measuring part 3, mounted on Z-table 122, moves to respective X, Y and Z directions. In additions a moving range toward respective directions of the measuring part 3 is configured so that the measuring optical system may be aligned to be the predetermined positional relationship with each of eyes considering individual difference of a size of a face and a position of eyes of a patient.

In FIG. 1, reference numeral 4 is a joystick which is used by the operator in case of the alignment operations the pulse motors 110a and 120a are driven by a signal caused by inclination of the joystick 4, thereby the measuring part 3 moves to X and Z directions. Also, the measuring part 3 moves to Y-direction based on a signal caused by rotation of a rotation knob 4a provided for the joystick 4. 5 is TV monitor for displaying an image of the patient's eye and information to be informed of the operators 6 is a printer for printing out the measured results. 7 is a switch group with which a switch for selecting either a right eye or a left eye, a print switch, a reset switch, a switch for selecting either a full-automatic alignment (a full-automatic alignment mode) or an operator's manual alignment (a manual mode) and the like are provided. Further, 8 is a measuring switch utilized for manual measurement by the operator.

Figure 4:
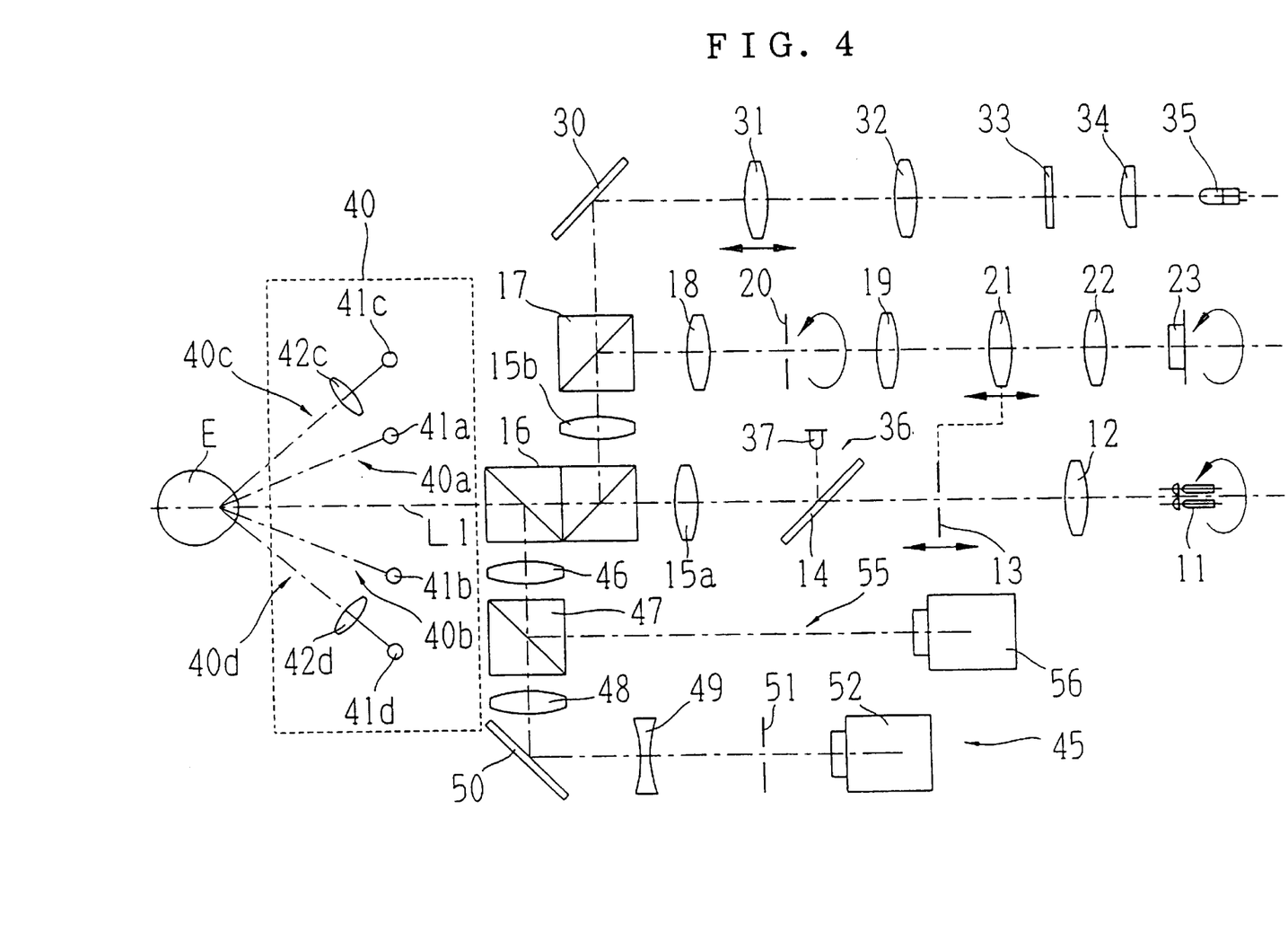
FIG. 4 is a top view showing a schematic construction of an optical system of the apparatus of the preferred embodiment of the present invention.

FIG. 4 is a view showing a schematic configuration of the optical system provided for the measuring part 3.

[The measuring optical system]

Reference numeral 11 is two light sources for measurement having wavelength of infrared range, which is disposed so as to rotate with the center at a measuring optical axis L1. 12 is a condenser lens, and the light source 11 is positioned at a focusing point in front of thereat. 13 is a target plate for measurement configured so as to move in order to be disposed at a conjugate position relative to a fundus of the eye E to be measured. 14 is a beam splitter, 15a is a projecting lens, 15b is an objective lens, 16 and 17 are beam splitters, 18 and 19 are relay lenses, 20 is a corneal reflection eliminating mask, being belt shaped, which is disposed at a conjugate position relative to a cornea of the eye E so that it may rotate with the center at the optical axis L1 being synchronized with the light source 11, 21 is a movable lens which moves together with the target plate 13 and 22 is a focusing lens. 23 is a photo-detector which rotates with the center at the optical axis L1 being synchronized with the light source 11 and the mask 20.

[The fixation target optical system]

Reference numeral 30 is a mirror, 31 is a first relay lens which fogs the eye E by moving on the optical axis, 32 is a second relay lens, 33 is a fixation target disposed at a focusing position of a second relay lens 32, 34 is a condenser lens, 35 is an illumination lamp for fixation target.

[The alignment target projecting optical system]

The alignment target projecting optical system consist of a first target projecting optical system 36 and a second projecting optical system 40.

The first target projecting optical system 36 is provided with a point light source 37 which emits infrared light and goes on and off periodically, and a beam splitter 14. Light flux from the point light source 37 is reflected by the beam splitter 14, then is made to be parallel luminous flux by the projecting lens 15a, and forms an image of the point light source by a corneal reflex of the eye E.

The second target projecting optical system 40 includes two target projecting optical systems 40a and 40b disposed so as to be symmetric with putting the optical axis L1 therebetween with forming the predetermined angle and two target projecting optical systems 40c and 40d disposed so as to be symmetric with putting the optical axis L1 therebetween with forming larger angle than the projecting optical systems 40a and 40b. The projecting optical systems 40a and 40b consist of point light sources 41a and 41b within infrared range, and project a target of finite distance onto the eye E. The projecting optical systems 40c and 40d consist of point light sources 41c and 41d within infrared range, and collimating lenses 42c and 42d, which project a target of infinite distance. Also, these projecting optical systems 40a to 40d are configured so that targets may be projected on the same meridian in a horizontal direction relative to the eye E.

[The alignment detecting optical system]

The alignment detecting optical system includes a first detecting optical system 45 and a second detecting optical system 55. The first detecting optical system 45 includes an objective lens 46, a beam splitter 47, relay lenses 48 and 49, a mirror 50, a telecentric diaphragm 51, and CCD camera 52, and detects a right eye and a left eye by photographing a face of the patient including both eyes with low magnification. Also, the first detecting optical system 45 is configured so as to photograph the face of the patient as if it is brought into focus even if a focusing direction is relatively rough by way of making the depth of field be deep by providing the telecentric diaphragm 51. The second detecting optical system 55 shares the objective lens 46 and the beam splitter 47 of the first detecting optical system 45, and photographs the eye E with high magnification by using CCD camera 56, thereby a target image projected onto the eye E by the alignment target projecting optical system is detected (in addition, referring to the preferred embodiments CCD camera having approximately 250,000 picture elements is adopted for CCD cameras 52 and 56).

In addition, the eye E photographed by the second detecting optical system 55 is illuminated with an infrared light source which is not shown, the face of the patient photographed by the first detecting optical system 45 is illuminated with a visible light source which is not shown.

Also, if the beam splitter 47 is changed to a dichloic mirror having characteristics of reflecting infrared-rays and transmitting visible-rays, then a fall of light volume for photography of CCD cameras 56 and 52 may be improved.

Figure 5:
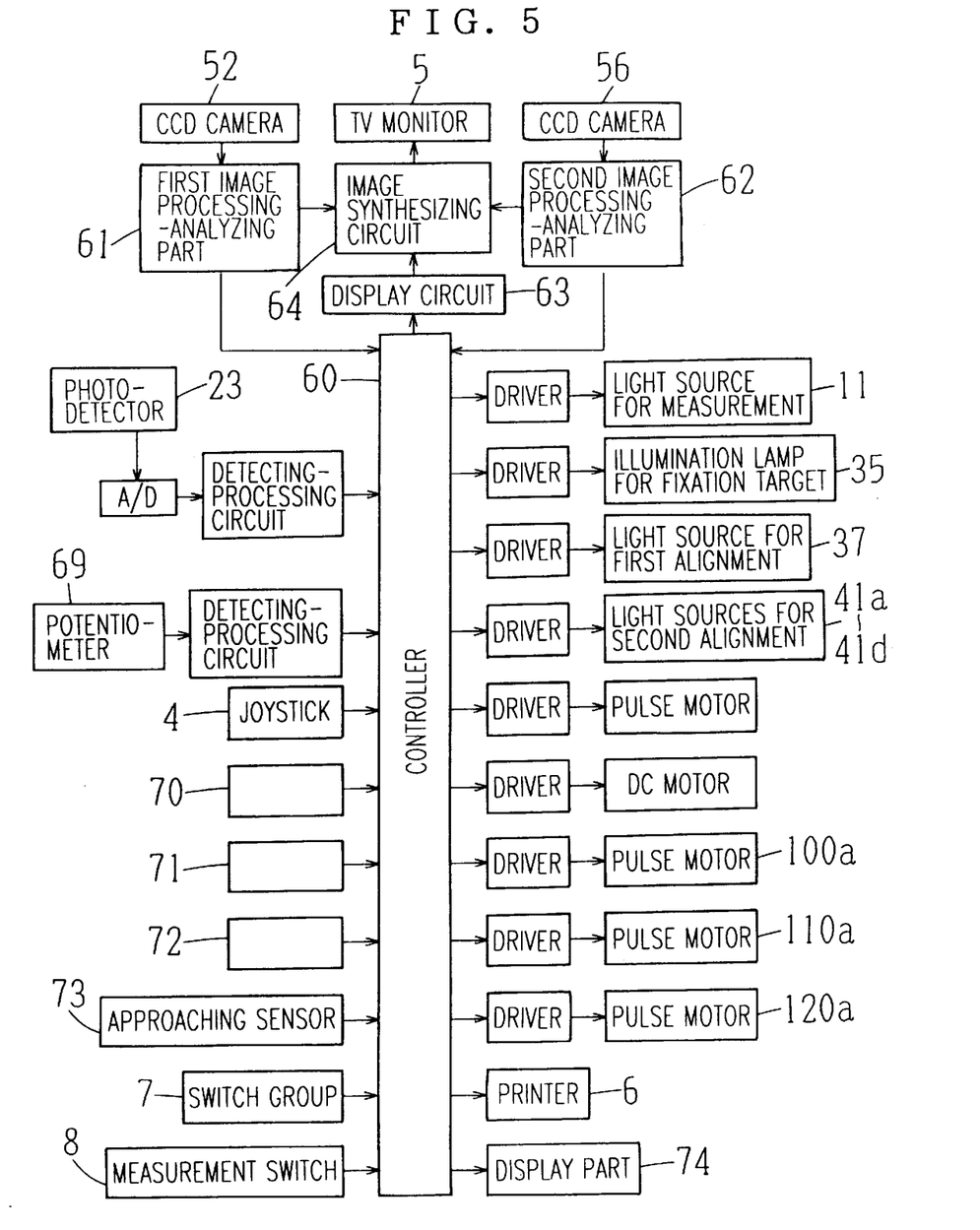
FIG. 5 is a view showing construction of an important part of a control system of the apparatus of the preferred embodiment of the present invention.

FIG. 5 is a view showing construction of an important part of a control system of the apparatus of the preferred embodiment. The first image processing-analyzing part 61 is connected to CCD camera 52, which specifies a right eye and a left eye and performs the analysis to obtain information for detecting the positional relationship of a right eye and a left eye with respect to the measuring optical axis L1. The second image processing-analyzing part 62 is connected to CCD camera 56, which performs the analysis to obtain information for detecting the positional relationship in X, Y and Z directions relative to the eye E based on the alignment target image caused by corneal reflex The information detected by the first image processing-analyzing part 61 and the second image processing-analyzing part 62 is inputted to a controller 60. The controller 60 drives the pulse motors 100a, 110a and 120a of respective moving mechanisms based on respective detected information, thereby moves the measuring part 3.

Image signals from CCD cameras 52 and 56 are inputted to an image synthesizing circuit 64 which synthesizes and changes-over an image displayed on TV monitor 5. A display circuit 63 which generates a reticle mark a figure, a character information and the like to be displayed on TV monitor 5 is connected to the image synthesizing circuit 64.

Figure 6:
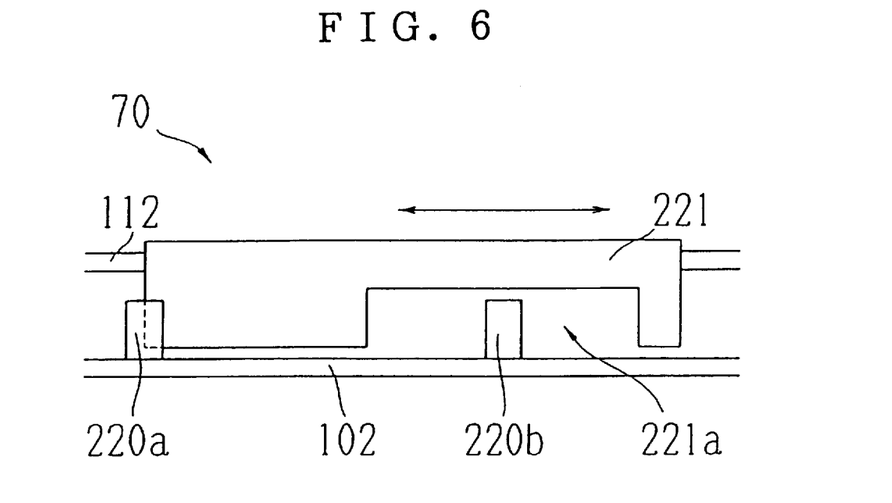
FIG. 6 is a view showing a mechanism for detecting a moving position in X direction.

X-movement positional detecting mechanism 70, Y-movement positional detecting mechanism 71 and Z-movement positional detecting mechanism 72 are connected to the controller 60, which detect the standard position and a movable limit in respective directions of the measuring part 3 relative to the body 1. As shown in FIG. 6, X-movement positional detecting mechanism 70 is provided with a photo-sensors 220a and 220b fixed to Y-table 102 and a shutter plate 221 having a notch 221a fixed to X-table 112. The photo-sensor 220a detects the standard position based on the timing of the change-over of the shuttering condition caused by an edge of the shutter plate 221, and detects which direction X-table 112 exists based on its shuttering condition. The photo-sensor 220b detects the moving limit of both sides based on the change-over of the shuttering condition of the notch 221a, caused by the movement of the shutter plate 221. Y and Z- movement positional detecting mechanisms 71 and 72 have the same construction as mentioned above, basically therefore, detect respective standard positions and moving limits by the same way. In addition, the standard position in X-direction is the center of the body 1, and the standard position in Y-direction is the center of the movable range. The standard position in Z-direction is the farthest side (side of the joystick 4) from the eye.

Figure 10:
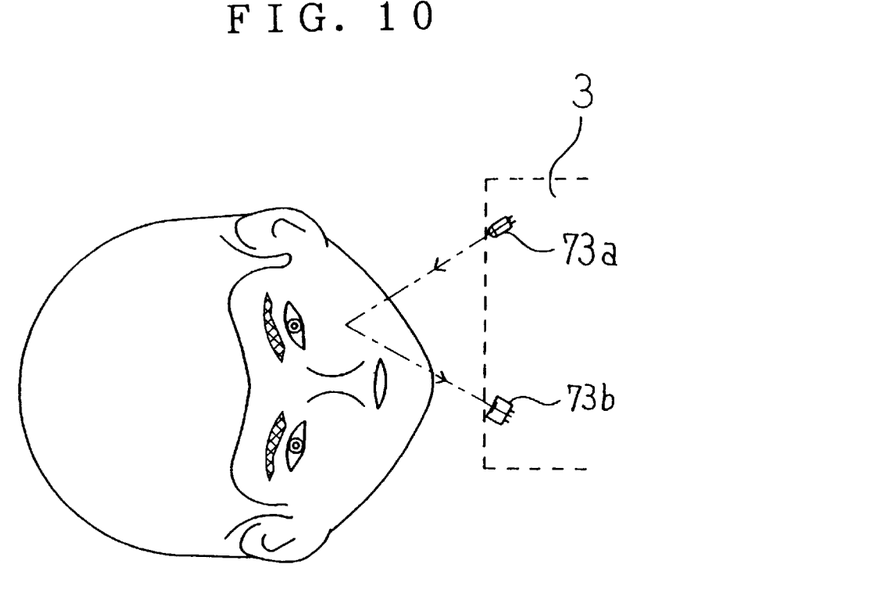
FIG. 10 is a view for illustrating a mechanism for detecting an approaching condition between the patient and the apparatus.

Reference numeral 73 is an approaching sensor fixed to the patient'side of the measuring part 3, which consists of an infrared-LED 73a and a photo-detector 73b (see FIG. 10). If the measuring part 3 approaches to the patient's face, then the reflex volume increases, therefore, when the light volume detected by the photo-detector 73b amounts to a certain value, the controller 60 stops the movement in Z-direction and prohibits the measuring part 3 from touching to the patient's face.

Next, the operation having such architecture will be described hereinafter. Firstly, the operation of a full-automatic alignment mode for which the operator's operation is not necessary will be described (see FIG. 11).

Figure 11:
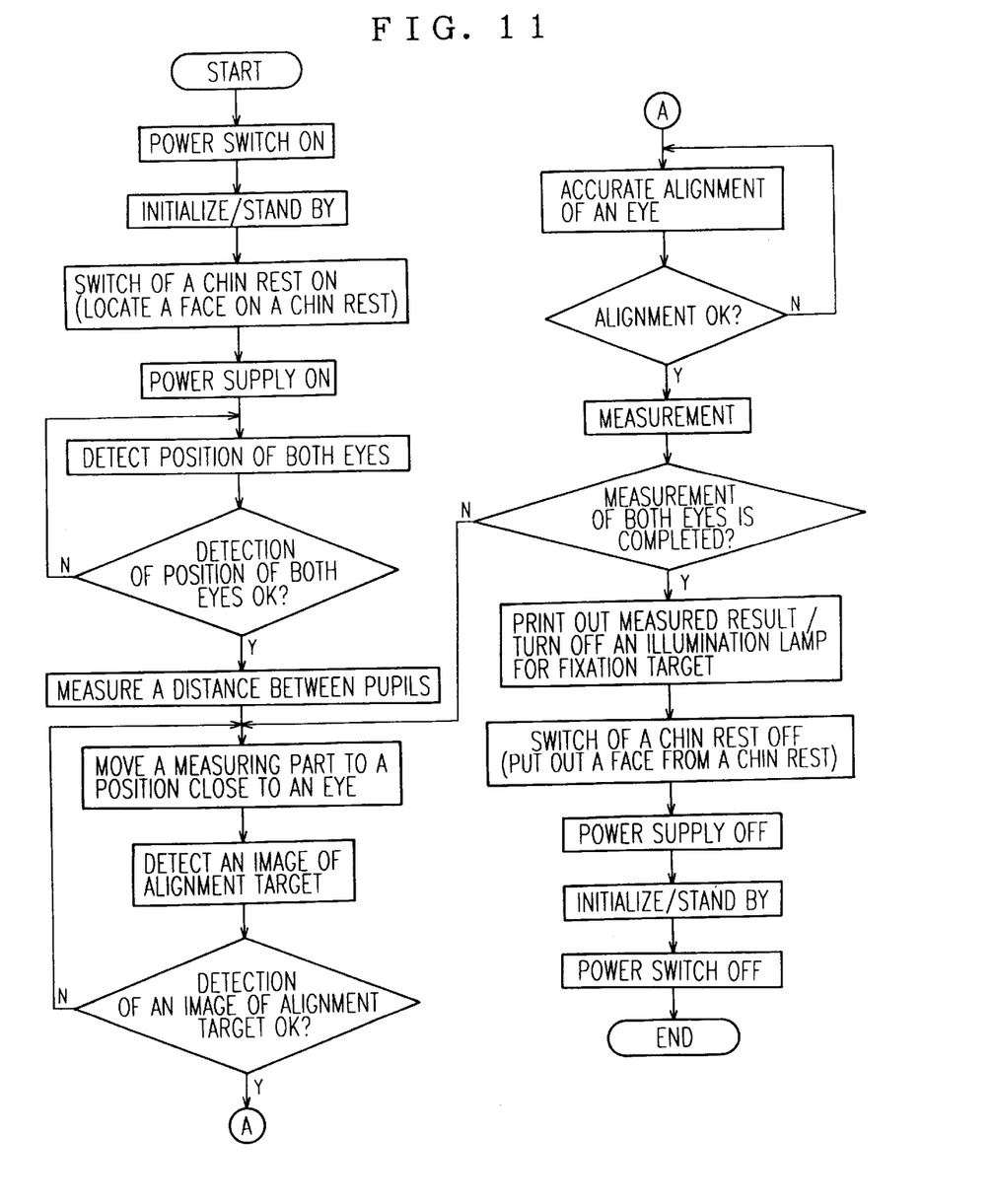
FIG. 11 is a flowchart for illustrating operation of the apparatus of the preferred embodiment of the present invention.

If the power switch is turned on, then the apparatus is initialized and the measuring part 3 is positioned at the standard position of respective directions so as to be standing by. When the patient's face is put on the chin rest 2a, then it is detected by the chin rest switch 2c. The controller 60 supplies power to respective parts, and enables the respective parts to work.

Figure 7:
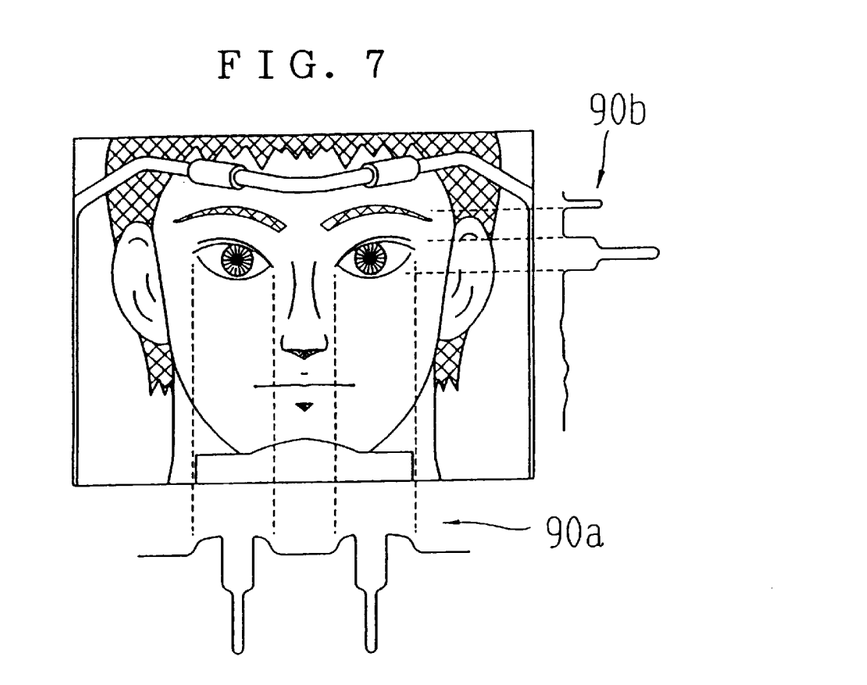
FIG. 7 is a view showing an image of a face of a patient including both eyes which are to be photographed by a detecting system of low magnification.

The apparatus performs the positional detection of both eyes of the patient as following, based on the image of low magnification photographed by CCD camera 52. As shown in FIG. 7, the patient's face including both eyes is photographed by CCD camera 52. The first image processing-analyzing part 61 extracts the edge from the image obtained by CCD camera 52. There is such characteristics that many edges exist in an eye-part relatively in a faces therefore, the eye's position can be approximately specified from the edge distributions 90a and 90b obtained by projecting the edge image data to horizontal and vertical directions respectively (even if many edges also appear in eyelash-part, they are differentiated by examining each shape of edge of respective horizontal and vertical directions). If the eye's position is specified, then the black part of the pupil is extracted on the basis of the light-and-shade information from the image close to its position. Around the eye, since the pupil is the darkest (black color) both eye s position on the image can be specified accurately. Also, since the photographing magnification is known already, the distance between both eyes (the distance between the pupils) can be calculated.

In addition, the positional detection of both eyes can be performed according to the change of image before and after the blink by processing and analyzing the image continuously The controller 60 calculates the deviation information of both eyes relative to the measuring part 3 (the optical axis Li) based on the information of the positional detection of both eyes, then moves the measuring part 3 to the right eye to be measured firstly (the eye to be measured firstly is designated in advance by the switch for selecting either a right eye or a left eye) in X and Y directions based on the deviation information. Thereby the measuring optical axis L1 is made to be positioned close to the right eye (the eye to be measured) of the patient. The eye to be measured (the right eye) becomes to look the fixation targets therefore, the eye looks at it. In addition, instead of designating the eye to be measured firstly, it can be controlled so that the nearer eye (of which the deviation is smaller than another one) to the measuring part 3 (the optical axis L1) may be the first eye to be measured.

When the movement is performed in X and Y directions, the alignment detection is changed-over to the target detection performed by CCD camera 56 and the second image processing-analyzing part 62, then the detection of the alignment target image projected onto the cornea of the eye is performed. At this time, Z direction of the measuring part 3 is deviated further than the appropriate working distance, therefore, the alignment target image is detected with forwarding the measuring part 3 relative to the eye. The controller 60 extracts the target image of the point light source 37 positioned at the center, among the alignment target images which are detected, then judges the alignment condition in X and Y direction with respect to the measuring optical axis L1. Also, judgement of the alignment condition in Z direction is performed by comparing heights (an interval between images) of the target image of infinite distance caused by the projecting optical systems 40c and 40d and the target image of finite distance caused by the projecting optical systems 40a and 40b. This utilizes such characteristics that in case of projecting the target of infinite distance and the target of finite distance, even if the working distance changes, then a height of the image (the interval between images) caused by the target of infinite distance does not change, however, a height of the image (the interval between images) caused by the target of finite distance changes (see Japanese Patent Laid-Open No.HEI6-46999 corresponding to U.S. Pat. No. 5,463,430).

The controller 60 performs the accurate alignment by moving the measuring part 3 to respective directions based on the target detecting information which is processed and analyzed by the second image processing-analyzing part 62. When the alignment condition of respective directions comes to be within the predetermined permissible range, and comes to be capable of measuring, then the controller 60 generates a trigger signal automatically and performs the measurement. In addition, at the time of measuring, the measured value may be corrected in accordance to the deviation of the alignment.

The target of the target plate 13 illuminated by the light source 11 for measurement is projected onto the eye, the target image reflected by the fundus is detected by the photo-detector 23. Then the target plate 13, as well as the movable lens 21, is made to move to be the conjugate position with the fundus of the eye, based on a signal of the fundus reflex received by the photo-detector 23. Next, the first relay lens 31 is made to move so that the eye may be fogged appropriate quantity of diopter, and the light source 11 for measurement and the photo-detector 23 are made to rotate 180° around the optical axis. While rotating, the target plate 13 moves based on a signal from the photo-detector 23, and the potentiometer 78 detects the amount of movement of the target plate 13, and calculates each value of the refractive power in respective meridian directions. The controller 60 gives the predetermined processing to the value of the refractive power, then obtains the refractive power of the eye. The measured results are displayed on the display part 74. In addition, the distance between both eyes (the distance between pupils) can be calculated at the time of measurement (before, during or after measurement) based on the image obtained by CCD camera 52 as described above. In this way, the focusing position is more accurate, therefore highly accurate value can be obtained.

When the measurement of the right eye is finished, the measuring part 3 is made to be moved to X and Y directions so that a left eye may be positioned close to the measuring optical axis L1 based on the distance (deviation) information calculated in advance. After that, as the same as the right eyes, the accurate alignment performed by the second image processing-analyzing part 62 based on the target detecting information is made to be completed, and the measurement is executed automatically. In case that the nearer eye to the measuring part 3 (the optical axis L1) is defined as the eye to be measured firstly, the positional adjustment is performed concerning the further eye based on the deviation information. In addition, whether the measurement of only one eye or the measurement of both eyes can be set in advance by using switches or the like.

When the measured results of one eye or both eyes are obtained, the controller 60 prints out the measured data from the printer 6, and turns off the illumination lamp 35 for fixation target. Thereby, the patient (and operator) can understand the finish of the measurement. In addition, the measurement finish can be also informed by voice or modulation of sound promised in advance, the lighting the lamp or the like. If the patient's face is put off from the chin rest 2a, the apparatus stops supplying useless power and performs initialization based on a detecting signal of the chin rest switch 2c, and returns to be standing by.

Figure 8:
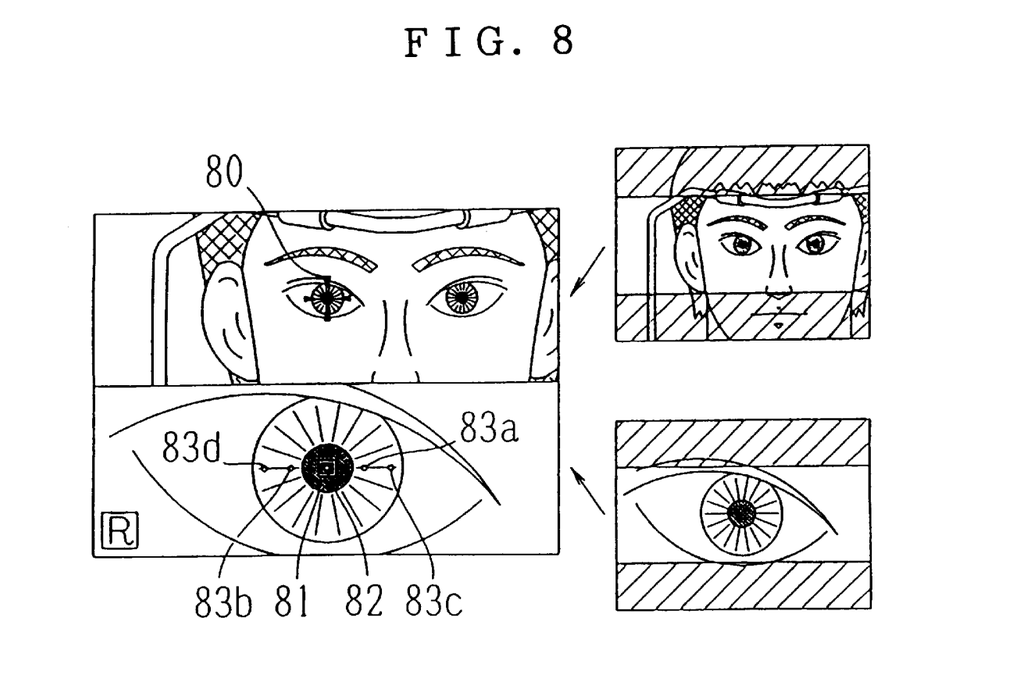
FIG. 8 is a view showing an example displaying an image of low magnification and an image of high magnification on the same screen.

Next, in case that the operator performs the alignment operation, the operation will be described hereinafter. Firstly, the manual mode is selected by using the selecting switch provided for the switch group 7. The apparatus performs initializations thereby the measuring part 3 is positioned at the standard position. The patient's face put on the chin rest 2a is photographed by CCD camera 52. The image synthesizing circuit 64 takes out ½ size of the central area from one screen of the photographed image, and displays the image of low magnification caused by CCD camera 52 on half above the monitor (on half below the monitor, ½ size of the central area of the image of high magnification photographed by CCD camera 56 is displayed).

The operator performs the alignment roughly by operating the joystick 4 with observing the image of the patient's face displayed on half above TV monitor 5 so that the patient's eye which is to be measured may come to the reticle mark 80. The controller 60 moves the measuring part 3 based on a signal corresponding to the inclining direction of the joystick 4 and a signal corresponding to the rotation of the rotation knob 4a. In addition, which eye is being aligned can be judged by detecting the position of right and left eyes automatically performed by the first image processing-analyzing part 61, therefore the switching operation for selecting either a right eye and a left eye is not necessary.

When the measuring part 3 is aligned roughly, the image of the eye photographed by CCD camera 56 becomes to be appear on half below TV monitor 5. The operator performs the alignment adjustment in X and Y directions with observing the image so that the target image 81 caused by the point light source 37 may be positioned at the center of the reticle mark 82 for use in the magnification alignment. Z direction is adjusted so that the target image 81 may be brought into focus The controller 60 has been detected the alignment condition based on a signal from the second image processing-analyzing circuit 62 as described above therefore, if an indicator indicating the moving direction of the measuring part 3 is made to be displayed on the screen, the alignment may be easier.

In addition, in case that it is difficult to observing the image by displaying the image of different magnification simultaneously on TV monitor 5, it can be configured so that the image may be changed-over automatically from the image of low magnification to the image of high magnification after the alignment target image can be detected.

Figure 9A:
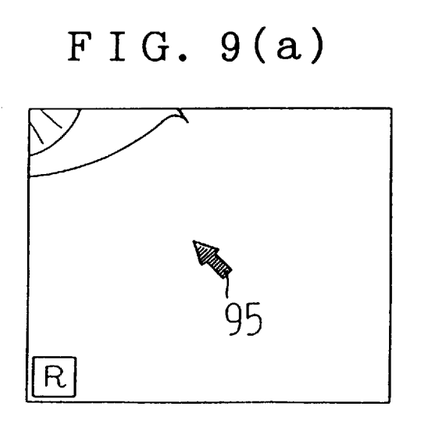
FIG. 9 is a view showing an example of a display for leading a measuring part to a moving direction.
Figure 9B:
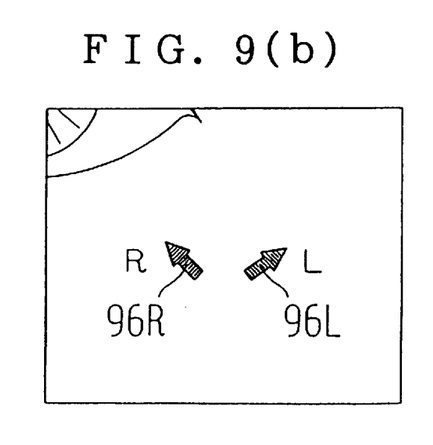

In addition, it can be configured that the image displayed on TV monitor 5 may be fixed to the image of high magnification, and an arrow leading the measuring part 3 to the moving direction may be displayed based on the information of the positional detection of right and left eyes. For example, it is designated in advance that which eye is to be aligned, and as shown in FIG. 9(a), an arrow 95 leading to the designated eye is displayed. Or, without designating in advance that which eye is to be aligned, as shown in FIG. 9(b), arrows 96R and 96L leading to respective right and left eyes. Thereby, even if the image of the patient's eye does not appear on the screen, the image of the eye can be found out easily by complying with the leading display.

When the alignment of the eye is completed, then the measurement is performed by depressing the measuring switch 8 (or the apparatus judges the suitability of the alignment, and performs the measurement automatically by generating the trigger signal.).

When the measurement of the one eye is finished, then the measurement of another eye is proceeded. As shown in FIG. 8, in case that two screens are displayed, the alignment operation is performed with observing the image of low magnification. In case that it is set that the image screen is changed-over between low and high magnification, when the target image comes not to be detected, the controller 60 changes-over the display screen from the image of high magnification to the image of low magnification. In addition, in case that the display screen is fixed to high magnification, the leading indicator of moving direction is displayed on the screen. Thereby, the operator performs the alignment adjustment for another eye, and the measurement is performed.

In above embodiment, the alignment detecting system having two optical paths of low and high magnification is utilized, however, if the CCD camera having high resolution, such as approximately 1,000,000 picture elements or more, is utilized for a detecting system of low magnification, then a detecting system of high magnification is not to be necessary.

In addition, it may be configured that the optical path which is photographed by CCD camera may be one, the optical system which changes the photographing magnification is made to be the change-over type, or the photographing magnification may be changed by a zoom lens.

In addition, in case of the measurement of full-automatic mode, to display the image on TV monitor 5 does not always necessary, therefore, simple one such as LED lamp, sound or the like, may be utilized for monitoring the suitability of the alignment condition and the measuring condition by the operator.

In addition, referring to above embodiment, the moving mechanism of the measuring part 3 is driven so that the automatic alignment may be possible, however, the apparatus of which the movable stand on which the measuring part is mounted is moved by the operation of the joystick relative to the fixation stand may be applied for the present invention.

In addition, if the patient's face is photographed by a photographing system of low magnification under the condition of wearing spectacles, and the positional information at the time of aligning with respective eyes is displayed in the image of low magnification, then the eye-point measurement may be possible. For example, the position of the eye-point relative to spectacles is measured by printing out the static picture with the eye-point, or by analyzing the image.

Figure 12:
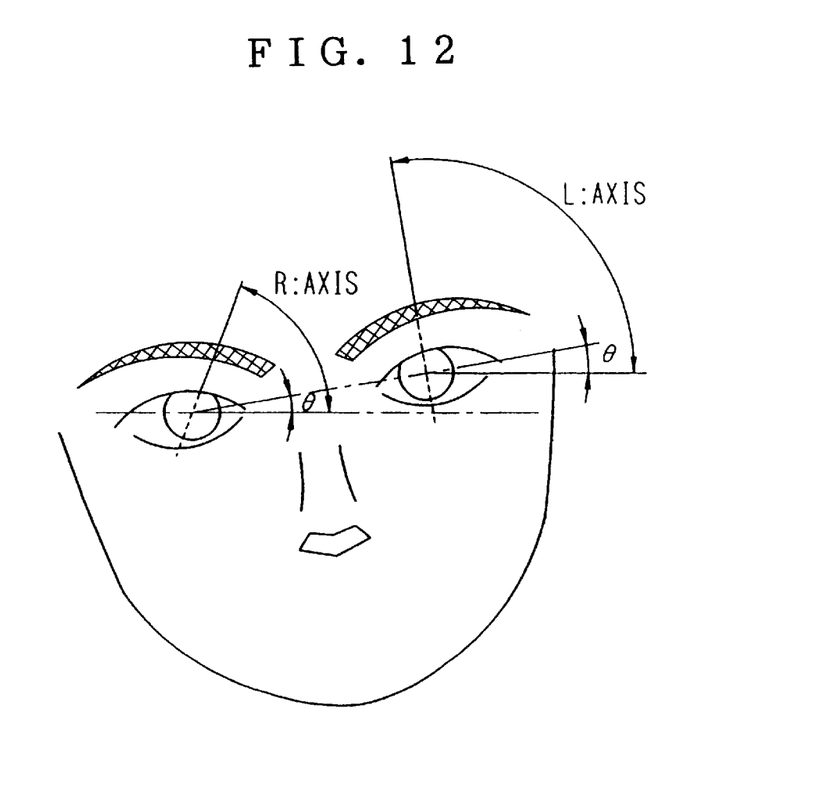
FIG. 12 is a view for illustrating correction of an astigmatism axial angle.

In addition, if the inclining angle of the patient's face is detected based on the positional detection of both eyes, then the astigmatism axial angle of the eye which is measured may be corrected. As described above, the pupil of both eyes can be extracted from the image photographed by CCD camera 52 of low magnification, therefore, the face-inclining angleθ is detected based on the line binding the centers of pupils (the center colored black) of right and left eyes and the horizontal line of CCD camera 52 (see FIG. 12) Referring to the measured result, the astigmatism axial angle (the astigmatism axial angle of right eye (R:AXIS), the astigmatism axial angle of left eye (L:AXIS)) of the eye which is measured can be obtained, therefore, if the inclining angleθ which is detected is subtracted from the astigmatism axial angle, then the accurate astigmatism axial angle can be calculated.

In addition, if each two of measuring optical system detecting optical system of high magnification and the like are prepared (in case of using CCD camera of high resolution, the detecting optical system of high magnification is not necessary), both eyes can be measured at the same time.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is the claimed is:

1. An ophthalmic apparatus comprising:
   measuring means for inspecting or measuring a patient's eye;
   moving means for moving said measuring means relative to the patient's eye;
   designating means for designating an eye to be measured;
   photographing means capable of photographing a face including both eyes of the patient;
   first detecting means for detecting positional relationship between said measuring means and each of right and left eyes respectively based on an image signal from said photographing means;
   alignment detecting means for detecting an alignment condition of said measuring means relative to the eye; and
   leading means for leading said moving means so that said measuring means may be alined within the predetermined range relative to the eye based on results detected by said first detecting means and said alignment detecting means.

2. The ophthalmic apparatus according to claim 1, wherein said designating means comprises input means for designating an eye to be measured.

3. The ophthalmic apparatus according to claim 1, further comprising:
   measurement finish detecting means for detecting a finish of measurement of one eye performed by said measuring means; whereby another eye not being the eye that measurement is finished being designated as an eye to be measured by said designating means at the time when it is detected by said measurement finish detecting means that the measurement of one eye is finished.

4. The ophthalmic apparatus according to claim 1, wherein said moving means comprises driving means for driving said measuring means electrically; and said leading means comprises movement controlling means for controlling said driving means based on results detected by said first detecting means and said alignment detecting means.

5. The ophthalmic apparatus according to claim 4, further comprising:

detecting means for detecting an approaching condition of said measuring means relative to a face of the patient; and regulating means for regulating the movement performed by said driving means so as not to approach excess the predetermined approaching condition, based on results detected by said detecting means.

6. The ophthalmic apparatus according to claim 1, wherein said moving means comprises operating parts to be operated by the operator, and said leading means comprises instructing means for instructing the operator which direction to move.

7. The ophthalmic apparatus according to claim 1, wherein said alignment detecting means comprising:

target projecting means for projecting an alignment target onto the eye; and second detecting means for detecting the alignment condition of said measuring means relative to the eye by detecting an image of the target projected by said target projecting means, whereby said moving means being led by said leading means so that said measuring means may be alined within the predetermined range relative to the eye based on results detected by said second detecting means.

8. The ophthalmic apparatus according to claim 7, wherein said second detecting means is served as said first detecting means by which detects the alignment condition of said measuring means relative to the eye by detecting the image of the target projected by said target projecting means based on the image signal from said photographing means; and said photographing means is one of high resolution.

9. The ophthalmic apparatus according to claim 1, wherein said first detecting means detects each position of both eyes based on continuous image signals from said photographing means according to the change of image before and after the blink of both eyes.

10. The ophthalmic apparatus according to claim 1, further comprising:

distance-between-pupils measuring means for obtaining a distance between pupils of both eyes based on the image signal from said photographing means according to the relationship between a photographing magnification and a photographing position of an image photographed by said photographing means.

11. The ophthalmic apparatus according to claim 1, further comprising:

angle measuring means for measuring an inclining angle of a face of the patient based on the image signal from said photographing means; and angle correcting means for correcting an astigmatism axial angle obtained by said measuring means based on the inclining angle obtained by said angle measuring means.

12. An ophthalmic apparatus comprising:

measuring means for inspecting or measuring a patient's eye;

moving means for moving said measuring means relative to the patient's eye;

designating means for designating an eye to be measured;

photographing means capable of photographing a face including both eyes of the patient;

first detecting means for detecting positional relationship between said measuring means and each of right and left eyes respectively based on an image signal from said photographing means;

first controlling means for controlling said moving means so that said measuring means may be alined close to the position of the eye designated by said designating means based on results detected by said first detecting means;

target projecting means for projecting an alignment target onto the eye under the condition that said measuring means is aligned close to the position of the eye;

second detecting means for detecting an alignment condition of said measuring means relative to the eye by detecting an image of the target projected by said target image projecting means;

second controlling means for further controlling said moving means so that said measuring means may be aligned to be capable of measuring based on results detected by said second detecting means;

judging means for judging suitability of the alignment based on results detected by said second detecting means; and measurement starting signal generating means for generating a starting signal for measurement, which causes said measuring means to work at the time when it is judged by said judging means that the alignment is appropriate.

13. The ophthalmic apparatus according to claim 12, wherein said designating means comprises input means for designating an eye to be measured.

14. The ophthalmic apparatus according to claim 12, further comprising:

measurement finish detecting means for detecting a finish of measurement of one eye performed by said measuring means; whereby another eye not being the eye that measurement is finished being designated as an eye to be measured by said designating means at the time when it is detected by said measurement finish detecting means that the measurement of one eye is finished.

15. The ophthalmic apparatus according to claim 12, further comprising:

detecting means for detecting an approaching condition of said measuring means relative to a face of the patient; and regulating means for regulating the movement performed by said driving means so as not to approach excess the predetermined approaching condition, based on results detected by said detecting means.

16. The ophthalmic apparatus according to claim 12, wherein said photographing means is a photographing means of high resolution; and said first detecting means is served as said second detecting means by detecting the alignment condition of said measuring means relative to the eye by detecting the image of the target projected by said target projecting means based on the image signal from said photographing means.

17. The ophthalmic apparatus according to claim 12, wherein said first detecting means detects each position of both eyes based on continuous image signals from said photographing means according to the change of image before and after the blink of both eyes.

18. The ophthalmic apparatus according to claim 12, further comprising:

distance-between-pupils measuring means for obtaining a distance between pupils of both eyes based on the image signal from said photographing means according to the relationship between a photographing magnification and a photographing position of an image photographed by said photographing means.

19. The ophthalmic apparatus according to claim 12, further comprising:

angle measuring means for measuring an inclining angle of a face of the patient based on the image signal from said photographing means; and angle correcting means for correcting an astigmatism axial angle obtained by said measuring means based on the inclining angle obtained by said angle measuring means.

* * * * *

UNITED STATES PATENT AND TRADEMARK OFFICE
CERTIFICATE OF CORRECTION

PATENT NO. : 5,909,269
DATED : June 1, 1999
INVENTOR(S) : ISOGAI et al.

It is certified that error appears in the above-identified patent and that said Letters Patent is hereby corrected as shown below:

Title page,

After "[22]  Filed:   Feb. 10, 1998" insert

--[30]    Foreign Application Data
    February 10, 1997    [JP]   Japan .......... 9-41475--

Signed and Sealed this

Twenty-ninth Day of August, 2000

Attest:

Attesting Officer

Q. TODD DICKINSON
Director of Patents and Trademarks